US005935069A

United States Patent [19]
Chandler et al.

[11] Patent Number: 5,935,069
[45] Date of Patent: Aug. 10, 1999

[54] ULTRASOUND SYSTEM AND METHOD FOR VARIABLE TRANSMISSION OF ULTRASONIC SIGNALS

[75] Inventors: Paul E. Chandler, Santa Cruz; David J. Block, San Jose, both of Calif.

[73] Assignee: Acuson Corporation, Mountain View, Calif.

[21] Appl. No.: 08/948,815

[22] Filed: Oct. 10, 1997

[51] Int. Cl.$^6$ .................................................. A61B 8/00
[52] U.S. Cl. ........................... 600/443; 600/458; 600/439
[58] Field of Search ................................. 600/453–458, 600/437, 443, 439

[56] References Cited

U.S. PATENT DOCUMENTS

| | | |
|---|---|---|
| 3,640,271 | 2/1972 | Horton . |
| 4,712,037 | 12/1987 | Verbeek et al. . |
| 5,040,537 | 8/1991 | Katakura ..................................... 601/2 |
| 5,111,823 | 5/1992 | Cohen . |
| 5,115,809 | 5/1992 | Saitoh et al. . |
| 5,135,000 | 8/1992 | Akselrod et al. . |
| 5,195,520 | 3/1993 | Schlief et al. . |
| 5,197,477 | 3/1993 | Peterson et al. . |
| 5,233,994 | 8/1993 | Shmulewitz . |
| 5,235,984 | 8/1993 | D'Sa . |
| 5,255,683 | 10/1993 | Monaghan . |
| 5,287,753 | 2/1994 | Routh et al. . |
| 5,313,948 | 5/1994 | Murashita et al. . |
| 5,358,466 | 10/1994 | Aida et al. . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,526,816 | 6/1996 | Arditi . |

(List continued on next page.)

FOREIGN PATENT DOCUMENTS

| | | |
|---|---|---|
| 0 357 164 | of 0000 | European Pat. Off. . |
| 0 770 352 A1 | 2/1997 | European Pat. Off. . |

OTHER PUBLICATIONS

Quantitation of Myocardial Perfusion With Contrast Echocardiography, American Journal of Cardiac Imaging, vol. 5, No. 3 (Sep.), 1991, pp. 200–216.

B. Schrope, et al., "Simulated Capillary Blood Flow Measurement Using A Nonlinear Ultrasonic Contrast Agent," Ultrasonic Imaging 14 (1992).

Chandra M. Sehgal, PhD., et al., "Sonographic Enhancement of Renal Cortex by Contrast Media." J. Ultrasound Med, 14; pp. 741–748 (1995).

(List continued on next page.)

Primary Examiner—Francis J. Jaworski
Attorney, Agent, or Firm—Brinks Hofer Gilson & Lione

[57] ABSTRACT

An ultrasound system and method for variable transmission of ultrasonic signals are presented. With this method and system, ultrasonic beams can be transmitted into a region in response to a selected event in a reference signal by predicting a future occurrence of a selected event in a reference signal, transmitting a first set of ultrasonic beams into the region at the predicted future occurrence, and transmitting a second set of ultrasonic beams into the region at a selected time interval preceding the predicted future occurrence. Additional applications of the method and system are presented.

18 Claims, 2 Drawing Sheets

U.S. PATENT DOCUMENTS

| | | |
|---|---|---|
| 5,540,909 | 7/1996 | Schutt . |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,685,310 | 11/1997 | Porter ..................................... 600/458 |
| 5,694,937 | 12/1997 | Kamiyama ............................. 600/458 |
| 5,709,210 | 1/1998 | Green et al. ............................ 600/455 |
| 5,735,281 | 4/1998 | Rafter et al. ............................ 600/458 |
| 5,740,807 | 4/1998 | Porter ..................................... 600/458 |
| 5,743,266 | 4/1998 | Levene et al. .......................... 600/458 |

OTHER PUBLICATIONS

Chandra M. Sehgal, PhD., et al., "Influence of Postprocessing Curves on Contrast–Echographic Imaging: Preliminary Studies" J. Ultrasound Med, 14; pp. 735–740 (1995).

Michael S. Longuet–Higgins, Resonance in nonlinear bubble oscillations. J. Fluid Mech. (1991) vol. 224.

Michalakis A. Averkiou, et al., "Self–demodulation of amplitude–and frequency–modulated pulses in a thermoviscous fluid." J. Acoustical Society of America, 94(5), Nov. 1993.

Nico de Jong, "Physical properties and technical aspects of ultrasound contrast agents."

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

Robert M. Lerner, et al., "'Sonoelasticity' Images Derived from Ultrasound Signals in Mechanically Vibrated Tissues." Ultrasound in Med. and Biol., vol. 16, No. 3, 1990.

Sharon L. Mulvagh, M.D., et al., "Abstract Session IV Contrast and Ischemia." Journal of the American Society of Echocardiography, vol. 8, No. 3, May 1995.

Samuel Gotlieb, M.D. et al., "Effect of Pressure on Echocardiographic Videodensity from Sonicated Albumin: An In Vitro Model." J. Ultrasound Med. 14 (1995).

"Supplement to Journal of the American College of Cardiology." American College of Cardiology, 45th Annual Scientific Session, Mar. 24–27, 1996 pp. 21A, 63A, 239–240A.

T.G. Leighton, "Transient excitation of insonated bubbles." Research Notes.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

V.L. Newhouse, et al., "Bubble size measurements using the nonlinear mixing of two frequencies." J. Acoust. Soc. Am. 75(5), May 1984.

Vokmar Uhlendorf, et al., "Nonlinear Acoustical Response of Coated Microbubbles in Diagnostic Ultrasound." IEEE 1994 Ultrasonics Symposium.

William Armstrong, M.D., et al., "American Society of Echocardiography Position Paper on Contrast Echocardiography." draft 1—Jun. 6, 1994.

Yang–Sub Lee, et al., "Time–domain Remodeling of pulsed finite–amplitude sound beams." J. Acoustical Society of America, 97(2), Feb. 1995.

Chiang c. Mei, et al., "Parametric resonance of a spherical bubble." J. Fluid Mech. (1991) vol. 229.

Deborah J. Rubens, M.D., "Sonoelasticity Imaging of Prostate Cancer: In Vitro Results." Radiology, vol. 195, No. 2, 1995.

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Fred Lee, Jr., M.D., "Sonoelasticity Imaging: Results in in Vitro Tissue Specimens." Radiology, vol. 181, No. 1 Oct. 1991.

H. Edward Karrer, et al., "A Phased Array Acoustic Imaging System for Medical Use." 1980 Ultrasonics Symposium.

"HP Ultrasound Technologies—Viability" About HP Ultrasound Imaging, WWW document 1997.

J. Ophir, et al., "Elastography: A Quantitative Method for Imaging the Elasticity of Biological Tissues." Ultrasonic Imaging 13, (1991).

J. W. Norris, "The non–linear oscillation of a radially symmetric bubble in a time periodic pressure field." Dynamics and Stability of Systems, vol. 9, No. 1 (1994).

J.A. Hossack, et al., "Improving transducer performance using multiple active layers." SPIE vol. 1733 (1992).

Janet B. Jones–Oliveira, et al., "Transient fluid—solid interaction of submerged spherical shells revisited: Proliferation of frequencies and acoustic radiation effects." Acoustical Society of America, 96(2) Pt. 1, Aug. 1994.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

K.J. Parker, et al., "Tissue Response to Mechanical Vibrations for 'Sonoelasticity Imaging'." Ultrasound in Med. & Biol., vol. 16, No. 3, (1990).

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Kevin J. Parker, PhD, et al., "Sonoelasticity of Organs: Shear Waves Ring a Bell." J. Ultrasound Med. 11 (1992).

Kotaro Sato, et al., "Numerical analysis of a gas bubble near a rigid boundary in an oscillatory pressure field." J. Acoustical Society of America, 95(5), May 1994.

L.W. Anson et al., "Ultrasonic scattering from spherical shells including viscous and thermal effects." J. Acoustical Society of America, 93(4), Apr. 1993.

Marc Gensane, "Bubble population measurements with a parametric array." 1994 Acoustical Society of America, 95(6) Jun.

Sample Interval 1:
    ECG Signal
    Independent Trigger
    Dependent Trigger
    Measured Value

Sample Interval 2:
    ECG Signal
    Independent Trigger
    Dependent Trigger
    Measured Value

Sample Interval 3:
    ECG Signal
    Independent Trigger
    Dependent Trigger
    Measured Value

Sample Interval 4:
    ECG Signal
    Independent Trigger
    Dependent Trigger
    Measured Value

ULTRASOUND SYSTEM AND METHOD FOR VARIABLE TRANSMISSION OF ULTRASONIC SIGNALS

BACKGROUND OF THE INVENTION

In medical ultrasound imaging, it is often desired to perform an ultrasound scan at a selected time interval. Typically, the scan is synchronized to a selected event that is referenced to a repeating signal on a reference signal. For example, a selected event may be 100 ms in advance of an R-wave on an ECG signal.

It is also often desired to perform two or more scans at different but related times. For example, an operator can transmit one set of ultrasonic beams to destroy or activate contrast agent in a region at a specific time before transmitting a set of ultrasonic beams to image the region. It has recently been recognized that there are benefits to interrupting scanning to either preserve contrast in the scan plane and/or to provide time for fresh contrast agent to flow into the scan plane before the next scan. Some of the benefits of suspending ultrasonic transmissions are described in U.S. Pat. No. 5,560,364 (Porter) and include improved sensitivity to contrast agents. In addition to performing two scans at different but related times, an operator may desire to trigger imaging after a specific amount of time has elapsed since the activation of a surgical tool such as a laser or an infusion pump.

When two or more events need to be synchronized, they are typically all synchronized directly to a repeating signal on a reference signal, such as an R-wave on an ECG signal. Because these repeating signals are unsteady and susceptible to slow or rapid drifts in period and to transient aberrant behavior, these synchronizing techniques provide inaccurate means for triggering the additional scans in many ultrasound applications.

SUMMARY OF THE INVENTION

The present invention is directed to an ultrasound system and method for variable transmission of ultrasonic signals. According to a first aspect of the invention, a method for transmitting ultrasonic beams in a region using a selected event in a reference signal is provided comprising the steps of predicting a future occurrence of a selected event in a reference signal, transmitting a first set of ultrasonic beams into the region at the predicted future occurrence, and transmitting a second set of ultrasonic beams into the region at a selected time interval preceding the predicted future occurrence.

According to a second aspect of this invention, a method for performing an ultrasound examination on a region comprising blood and contrast agent is provided. This method comprises the steps of transmitting a first set of ultrasonic signals into the region to create a reduced concentration of operative contrast agent and transmitting a second set of ultrasonic signals into the region to image the contrast agent in the region. One of these steps is synchronized with a predicted future occurrence of a selected event in a reference signal and the other is performed at a selected time interval preceding the predicted future occurrence. Instead of contrast destruction, contrast activation can be used.

According to a third aspect of this invention, another method for performing an ultrasound examination on a region comprising blood and contrast agent is provided. This method comprises the steps of transmitting a first set of ultrasonic signals into the region to create a reduced concentration of operative contrast agent, and transmitting a second set of ultrasonic signals into the region to measure a concentration level of contrast agent in the region. One of these steps is synchronized with a predicted future occurrence of a selected event in a reference signal and the other step is performed at a first time interval preceding the predicted future occurrence. These steps are repeated with varying time intervals. As with the method described above, contrast activation can also be used instead of contrast destruction.

According to a fourth aspect of this invention, a method for physio-signal activation of a surgical tool is provided. This method comprises the steps of predicting a future occurrence of a selected event in a reference signal, transmitting a set of ultrasonic beams into a region at the predicted future occurrence, and activating a surgical tool to perform an action in the region at a selected time interval preceding the predicted future occurrence.

Ultrasound systems that can perform each of the above methods are also provided.

DETAILED DESCRIPTION OF THE PRESENTLY PREFERRED EMBODIMENTS

In describing the preferred embodiments, several terms will be used. As used herein, "a selected event" describes an event in a reference signal that initiates an independent trigger; an "independent trigger" is a trigger that occurs at the selected event; a "dependent trigger" is a trigger that is timed in advance of the independent trigger; and a physio signal is any reference signal of a patient, such as an ECG or respiration signal.

Figure 1:
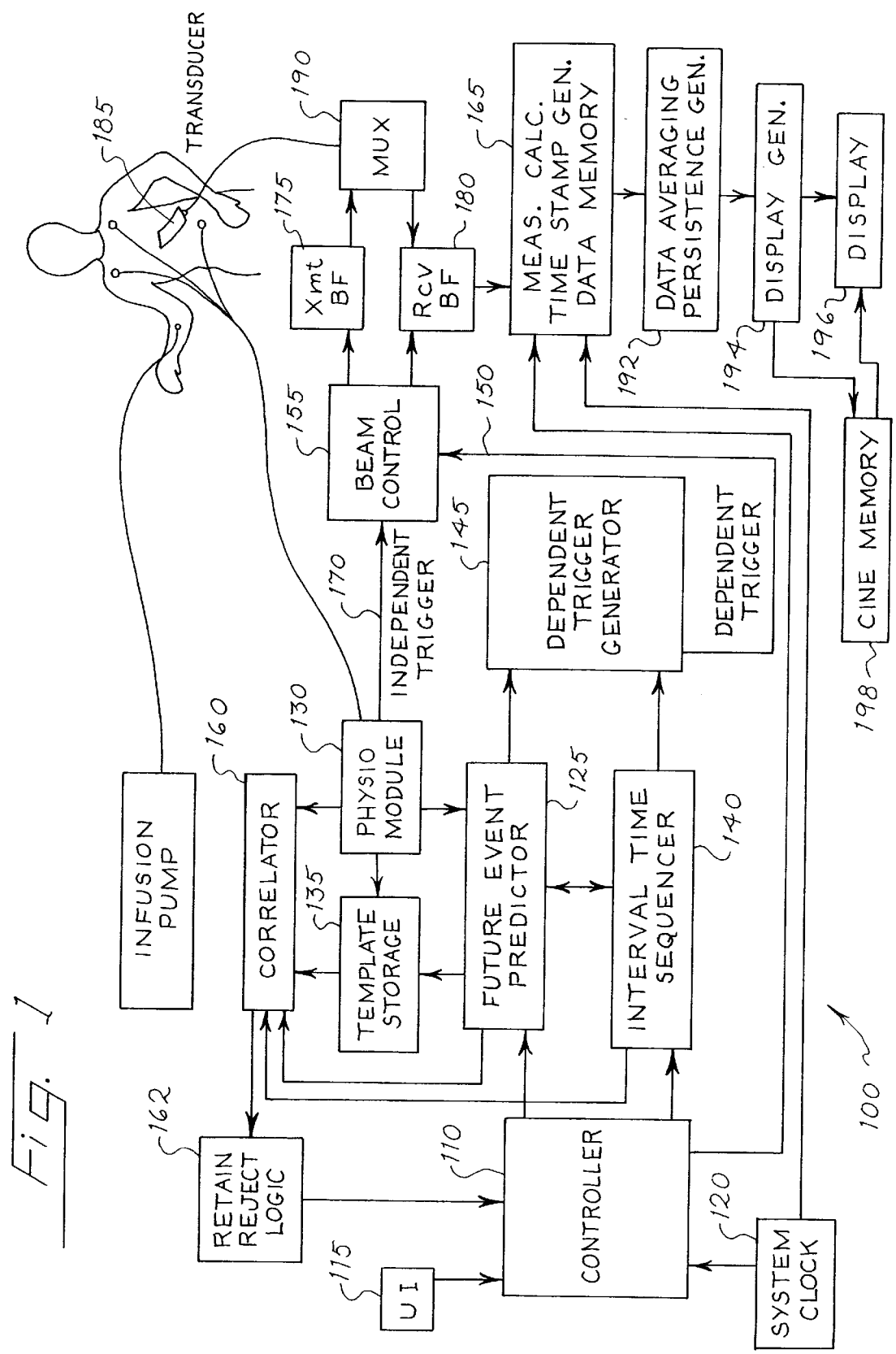
FIG. 1 is a block diagram of an ultrasound imaging system of a preferred embodiment.
Figure 2:
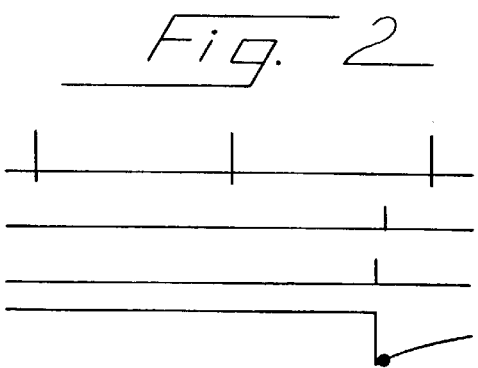
FIG. 2 is a timing chart that illustrates a method of a preferred embodiment operating at a first interval.
Figure 3:
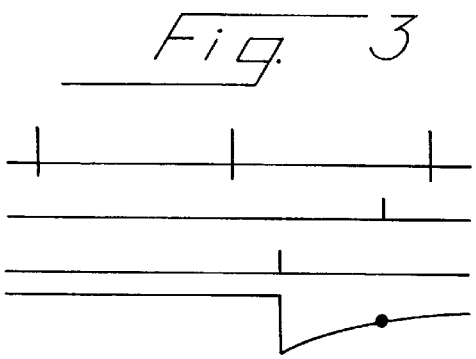
FIG. 3 is a timing chart that illustrates a method of a preferred embodiment operating at a second interval.
Figure 4:
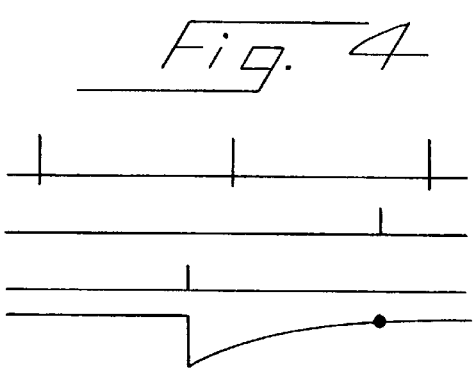
FIG. 4 is a timing chart that illustrates a method of a preferred embodiment operating at a third interval.
Figure 5:
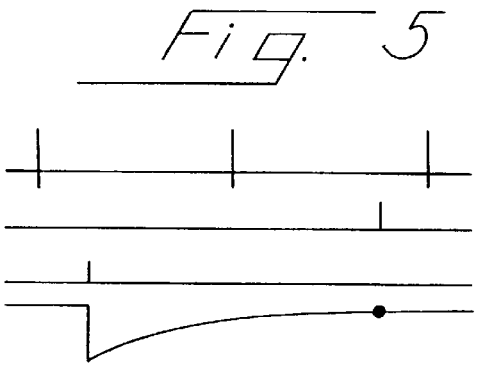
FIG. 5 is a timing chart that illustrates a method of a preferred embodiment operating at a fourth interval.

Turning now to the figures, FIG. 1 is a block diagram of an ultrasound system 100 of a preferred embodiment. Several preferred features of this system 100 will be described below to illustrate the function of several of the components shown in FIG. 1. It is important to note that this is merely one embodiment and a system of another embodiment can comprise more or fewer features. For example, one embodiment can comprise means for predicting a future occurrence of a selected event in a reference signal, transmitting a first set of ultrasonic beams into the region at the predicted future occurrence, and transmitting a second set of ultrasonic beams into the region at a selected time interval preceding the predicted future occurrence.

In illustrating this system 100, an R-wave in an ECG reference signal is used, but any regularly occurring signal in any reference signal can be used in operation. Also, the system is illustrated in the context of measuring and reducing a concentration of contrast agent in a region. It is important to note that other applications, including but not limited to the preferred methods described below, can be implemented. It is only the following claims, including all equivalents, that are intended to define the scope of this invention.

Returning to the system 100 of FIG. 1, a controller 110 accepts operator commands through a user interface 115 and receives signal clock values from a system clock 120. To initiate the methods described below, the operator enters a "physio signal reference template" mode and selects at least one portion of the physio signal to be used for comparison with the real time physio signal during real time scanning. The physio signal is frozen when entering the "physio signal reference template" mode, and two cursors are provided to the user to be positioned on the frozen physio signal. The first of these cursors selects the start point of the reference template, and the second cursor selects the end point of the template, which is also the point at which the independent trigger is to be generated. When more than one physio signal are made available, templates for all physio signals can be acquired simultaneously for concurrent time periods using the cursor placement method described above. The user can select which of the physio signals to use.

A future event predictor 125 controls selection of templates using data supplied by a physio module 130 and stored in a template storage unit 135. Also stored in the template storage unit 135 is the n cycle R-wave interval average determined just prior to freezing the physio module 130 for template acquisition and the time between the closest R-wave preceding the second cursor and the second cursor. Several processes run simultaneously during real time scanning, namely future event prediction, future event selection, future event validation, and scanner control, each of which is described below.

Future Event Prediction

During future event prediction, a future event predictor 125 tracks the R-wave interval and, based on the n cycle average of recent R-wave intervals, predicts the timing of subsequent R-waves. It then adds the time separation between the R-wave and second wave cursor stored during template acquisition to the estimated R-wave to determine the estimated times at which the desired trigger event, marked by the second cursor, will occur on each period of the physio signal in the near future.

Future Event Selection

During future event selection, an interval time sequencer 140 receives estimated times for the future occurrence of both R-waves and independent triggers, based on a predetermined data acquisition strategy programmed into the interval time sequencer 140 and modifying parameters made available via the user interface 115 and the controller 110. The interval time sequencer 140 selects future independent trigger times at which measurement scans are to be conducted out of the set of potential independent trigger times calculated and sent to it by the future event predictor 125. It then determines the correct timing for the next pair of independent and dependent triggers and sends a request for dependent trigger timing to the dependent trigger generator 145. The dependent trigger generator 145, in turn, generates a dependent trigger 150, sending it to the beam control unit 155. It sends the request for independent trigger timing to the correlator 160, which also receives estimated future times for both R-waves and independent trigger times. The request for independent trigger timing to the physio moduler 130, which generates the independent trigger 170 at the appropriate R-wave, is also sent.

Future Event Validation

The stored templates from the template storage unit 135, the real time physio signals from the physio module 130, the desired future time for the next independent trigger, and the estimated times for the near future R-waves and independent triggers are available to the correlator 160. During real time scanning, the correlator 160 remains idle until the time at which the independent trigger was selected to occur. In this illustration, a measurement scan is then initiated by the physio module 130. At this time, the correlator 160 compares the previous n cycle R-wave interval average to the average value stored in the template storage unit 135. A valid state is generated if the averages vary by less than a user selected tolerance. If an R-wave valid state is generated, the correlator 160 then compares the stored physio signal reference template with the current real time physio signal sampled at the predetermined independent trigger point. If the correlation is within user selected limits, another valid state is generated and is then passed to retain/reject logic 162. If the retain/reject logic 162 receives a valid state it sends a stored data signal to the controller 110. Otherwise, a discard and repeat signal is sent. These signals cause the appropriate actions according to their names. The store reject/signal is sent to the interval time sequencer 140 and to the measurement calculator/time stamp generator/and data memory 165 by the controller 110.

Scanner Control

The beam control unit 155 receives dependent triggers 150 and independent triggers and then generates and transmits beam control instructions to the transmit beamformer 175 and the receive beamformer 180, which in turn send and receive signals from the transducer 185 via the multiplexer 190. Received signals pass through a measurement calculator/time stamp generator/and data memory 165 where they are either rejected or saved and passed onto the data averaging/persistence engine 192, where they are averaged or temporally persisted before transmission to the display generator 194 and display 196. Output from the display generator 194 may also be sent to CINE memory 198 for later presentation on the display 196. It is also possible to send retained and rejected measurement data through to the display 196 to assist the operator in resolving setup and measurement issues during a study.

There are several methods which can be implemented with the system 100 described above and its various embodiments. One preferred method takes advantage of the recent advance in ultrasound of interrupting scanning to either preserve contrast in the scan plane and/or to provide time for fresh contrast agent to flow into the scan plane before the next scan. Specifically, a first set of ultrasonic signals can be transmitted into a region in a patient to disrupt contrast agent in the region to create a reduced concentration of operative contrast agent. The first set can be transmitted into the region at a selected time interval preceding the predicted future occurrence by using the process of generating a dependent trigger described above.

To take full advantage of the improved imaging resulting from reducing the concentration of contrast agent, it is preferred that imaging of the region occur at a specific time after reduction. That is, it is preferred that imaging be performed at a fixed time past the time of contrast agent reduction. Accordingly, a second set of ultrasonic signals can be synchronized with a predicted future occurrence of a selected event in a reference signal (e.g., synchronized with a point referenced to an R-wave of an ECG signal that indicates when an independent trigger is to be generated). The power of the ultrasonic beams of the second set is preferably lower than the power of the beams of the first set to limit contrast agent disruption. By using this method, the operator can maximize the benefits of improved sensitivity to contrast agents.

Another preferred method finds application when using ultrasound beams in making measurements in a region whose concentration of contrast agent has been reduced. As with the above method, a first set of ultrasonic signals can be transmitted into a region to reduce the concentration of operative contrast agent. This transmission can occur at a selected time interval preceding the predicted future occurrence by using the process of generating a dependent trigger described above. A second set of ultrasonic signals can be transmitted into the region to measure the concentration level of contrast agent a specific time after reduction. This second set is synchronized with a predicted future occurrence of a selected event in a reference signal (e.g., synchronized with a point referenced to an R-wave of an ECG signal that indicates when an independent trigger is to be generated). The power of the ultrasonic beams of the second set is preferably lower than the power of the beams of the first set to limit contrast agent disruption.

When taking concentration level measurements, many samples at different time intervals are often required to sample a rapidly evolving transient process. Existing ultrasound systems cannot sample rapidly evolving transients while maintaining imaging at a fixed event point in the reference signal. If the transient process evolves completely within a few periods of the cycle, and if the measurement scan must be fixed to a single event in an ECG signal, only a few data samples will be available. Accordingly, for rapid transients, acquiring one sample per period of the reference signal may only yield two or three data samples—an amount which will often not provide a meaningful measurement.

To collect enough data, a plurality of cycles of reducing concentration of operative contrast agent in a region and imaging the region can be used. For example, a set of ultrasonic beams that will reduce the concentration level of contrast agent in the region can be fired 300 ms before the R wave on an ECG trace. Subsequent measurements may adjust the 300 ms time period at predetermined intervals, say 100 ms intervals, over a range of times between perhaps 0 ms and 3 secs in advance of the selected R wave. The time interval can increase or decrease from one cycle to the next and can be greater than the period of a regularly occurring signal in the reference signal.

FIGS. 2–5 illustrate the data collection process described above. With each interval in FIGS. 2–5, the dependent trigger moves ahead of the independent trigger on subsequent acquisition cycles. This moves the measured function relative to the independent trigger and affects the measured value at the independent trigger. If the measured function extends multiple intervals of the physio signal, ECG in this example, measurements can be conducted at the independent trigger on every interval for a preselected number of intervals sufficient to study the measured function providing more than one data sample per acquisition cycle. Note that all data samples from a single acquisition cycle are separated in time by one period of the ECG. Also note that by adding all data sets acquired with sample intervals shown in FIGS. 2–5, a data set covering two cardiac cycles and sampled twice per ECG period is created. The same data could be acquired using only two acquisition cycles if another independent trigger were fired on the next R-wave interval (not shown) in the acquisition cycles of FIGS. 2 and 3 and the two sets were added. Both strategies provide four sample points spaced at half ECG intervals. The second provides this data in half the time. The data collected using this method can later be merged into a single data set that is finely sampled in time, providing a meaningful measurement.

As mentioned above, this method is particularly useful in calculating perfusion into a region of a tissue, as described in U.S. patent application Ser. No. 08/949,237, hereby incorporated by reference, which is assigned to the assignee of the present invention. When calculating perfusion, typical ultrasound systems are unable to collect a necessary number of data samples to perform the calculation. The method described above permits sampling of reperfusion on successive cycles when reperfusion occurs too rapidly to be measured over several cycles of the tissue motion.

Although the above illustrates the advantage of using methods with contrast agent, the embodiments described above can be used when perform successive image or measurement scans. For example, a preferred method comprises the steps of predicting a future occurrence of a selected event in a reference signal, transmitting a first set of ultrasonic beams into the region at the predicted future occurrence, and transmitting a second set of ultrasonic beams into the region at a selected time interval preceding the predicted future occurrence.

Another preferred method relates to physio-signal activation of a surgical tool before an anticipated transmission of a set of ultrasonic beams. This method comprises the steps of predicting a future occurrence of a selected event in a reference signal, transmitting a set of ultrasonic beams into a region at the predicted future occurrence, and activating a surgical tool to perform an action in the region at a selected time interval preceding the predicted future occurrence. As used herein, surgical tool refers to any surgical device that can be used in conjunction with an ultrasound examination. Surgical devices include, but are not limited to, infusion pumps and inter-operative tools such as a laser. This method can be used, for example, when it is desired to acquire an image at a fixed point in the cardiac cycle following the firing of a laser into a blood clot for the purposes of clot ablation. As another example, this method can be used to image a region after an infusion pump injects a patient with an amount of contrast agent.

It may be preferred to track the tissue of interest as it moves relative to the transducer due to cardiac or respiration effects. Tracking moving tissue is known in the art and is described in U.S. patent application Ser. No. 08/916,358, which is assigned to the assignee of the present invention. By tracking the tissue, the ultrasound system can transmit sets of ultrasonic beams in the appropriate location.

In an alternative embodiment, instead of disrupting contrast agent in the region, contrast agent can be activated by a set of ultrasonic signals. As used above, operative contrast agent signifies contrast agent that is effective to return an enhanced echo signal, either at the fundamental or the harmonic frequency. Disrupted contrast agent signifies contrast agent that has been destroyed or otherwise modified such that it returns a substantially reduced or negligible echo signal. Also as used herein, a set of ultrasound signals includes signals associated with one or more transmit events that create a region of disrupted contrast agent or region of activated contrast agent or that provide an image or measurement of a selected region of the tissue.

Additional details regarding contrast agent imaging can be found in U.S. patent application Ser. No. 08/916,163, hereby incorporated by reference, which is assigned to the assignee of the present invention.

It is intended that the foregoing detailed description be understood as an illustration of selected forms that the invention can take and not as a definition of the invention. It is only the following claims, including all equivalents, that are intended to define the scope of this invention.

What is claimed is:

1. A method for transmitting ultrasonic beams in a region using a selected event in a physio reference signal of a patient, said method comprising the steps of:
   (a) predicting a future occurrence of a selected event in a physio reference signal of a patient;
   (b) determining a future occurrence of a second event by subtracting a selected time interval from the predicted fixture occurrence of the selected event;
   (c) transmitting a first set of ultrasonic beams into the region at the second event; and
   (d) transmitting a second set of ultrasonic beams into the region at the predicted future occurrence of the selected event.

2. A method for performing an ultrasound examination on a region comprising blood and contrast agent, said method comprising the steps of:
   (a) predicting a future occurrence of a selected event in a physio reference signal of a patient;
   (b) determining a future occurrence of a second event by subtracting a selected time interval from the predicted future occurrence of the selected event;
   (c) transmitting a set of higher power ultrasonic signals into the region, said set of higher power ultrasonic signals operative to selectively disrupt the contrast agent in the region to create a reduced concentration of operative contrast agent; and
   (d) transmitting a set of lower power ultrasonic signals into the region to image the contrast agent in the region, said set of lower power ultrasonic signals disrupting the contrast agent to a lesser extent than the set of higher power ultrasonic signals;
   one of steps c or d being synchronized with the predicted future occurrence of the selected event and the other of steps c or d being performed at the second event.

3. A method for performing an ultrasound examination on a region comprising blood and contrast agent in a body, said method comprising the steps of:
   (a) predicting a future occurrence of a selected event in a physio reference signal of a patient;
   (b) determining a future occurrence of a second event by subtracting a selected time interval from the predicted future occurrence of the selected event;
   (c) transmitting a set of higher power ultrasonic signals into the region, said set of higher power ultrasonic signals operative to selectively activate the contrast agent in the region to create an enhanced concentration of operative contrast agent; and
   (d) transmitting a set of lower power ultrasonic signals into the region to image the contrast agent in the region, said set of lower power ultrasonic signals activating the contrast agent to a lesser extent than the set of higher power ultrasonic signals;
   one of steps c or d being synchronized with the predicted future occurrence of the selected event and the other of steps c or d being performed at the second event.

4. A method for performing an ultrasound examination on a region comprising blood and contrast agent, said method comprising the steps of:
   (a) predicting a future occurrence of a selected event in a physio reference signal of a patient;
   (b) determining a future occurrence of a second event by subtracting a first time interval from the predicted future occurrence of the selected event;
   (c) transmitting a set of higher power ultrasonic signals into the region, said set of higher power ultrasonic signals operative to selectively disrupt the contrast agent in the region to create a reduced concentration of operative contrast agent; and
   (d) transmitting a set of lower power ultrasonic signals into the region to measure a concentration level of contrast agent in the region, said set of lower power ultrasonic signals disrupting the contrast agent to a lesser extent than the set of higher power ultrasonic signals, one of steps c or d being synchronized with the predicted future occurrence of the selected event and the other of steps c or d being performed at the second event; and
   (e) repeating steps (a) through (d) at a second time interval.

5. A method for performing an ultrasound examination on a region comprising blood and contrast agent in a body, said method comprising the steps of:
   (a) predicting a future occurrence of a selected event in a physio reference signal of a patient;
   (b) determining a future occurrence of a second event by subtracting a first time interval from the predicted future occurrence of the selected event;
   (c) transmitting a set of higher power ultrasonic signals into the region, said set of higher power ultrasonic signals operative to selectively activate the contrast agent in the region to create an enhanced concentration of operative contrast agent; and
   (d) transmitting a set of lower power ultrasonic signals into the region to measure a concentration level of contrast agent in the region, said set of lower power ultrasonic signals activating the contrast agent to a lesser extent than the set of higher power ultrasonic signals, one of steps c or d being synchronized with the predicted future occurrence of the selected event and the other of steps c or d being performed at the second event; and
   (e) repeating steps (a) through (d) at a second time interval.

6. The method of claim 4 or 5, wherein the measured concentration level is used to calculate perfusion of said region.

7. The method of claim 4 or 5, wherein the second time interval is greater than the first time interval.

8. The method of claim 4 or 5, wherein the second time interval is less than the first time interval.

9. The method of claim 4 or 5, wherein the second time interval is greater than a period of a regularly occurring signal in the reference signal.

10. A method for physio-signal activation of a surgical tool before an anticipated transmission of a set of ultrasonic beams, said method comprising the steps of:
    (a) predicting a future occurrence of a selected event in a physio reference signal of a patient;
    (b) determining a future occurrence of a second event by subtracting a selected time interval from the predicted future occurrence of the selected event;
    (c) transmitting a first set of ultrasonic beams into the region at the second event; and
    (d) activating a surgical tool to perform an action in the region at the predicted future occurrence of the selected event.

11. The method of claim 1, 2, 3, 4, 5, or 10, wherein the future occurrence of said selected event is predicted by performing the steps of:

calculating a time difference between the selected event and a first regularly occurring signal in said reference signal; and adding said time difference to a second regularly occurring signal in said reference signal.

12. The method of claim 1, 2, 3, 4, or 5 further comprising the steps of:

(d) calculating a difference between a first and a second occurrence of a regularly occurring signal in said reference signal; and (e) re-transmitting both sets of ultrasound beams in response to said difference exceeding a selected threshold.

13. The method of claim 12, wherein said regularly occurring signal is an R-wave and wherein said reference signal is an ECG signal.

14. The method of claim 12 further comprising the step of:

(f) calculating a time difference between an occurrence of a selected event and a predicted future occurrence of said selected event, each with respect to a regularly occurring signal in the reference signal; and (g) re-transmitting both sets of ultrasound beams in response to said time difference in step (f) exceeding a selected threshold.

15. The method of claim 1, 2, 3, 4, 5, or 10, wherein said reference signal is a respiration signal.

16. The method of claim 1, 2, 3, 4, 5, or 10, wherein said reference signal is an ECG signal.

17. In an ultrasound imaging system comprising a transmit beamformer, a receive beamformer, a transducer responsive to the transmit beamformer and coupled to the receive beamformer, and means for providing a physio reference signal, the improvement comprising:

means, responsive to the reference signal, for predicting a future occurrence of a selected event in the reference signal;

means, responsive to the reference signal, for determining a future occurrence of a second event by subtracting a first time interval from the predicted future occurrence of the selected event;

means, coupled to the transmit beamformer for transmitting a first set of ultrasonic beams into the region at the second event, and means, coupled to the transmit beamformer, for transmitting a second set of ultrasonic beams into the region at the predicted future occurrence.

18. The invention of claim 17 further comprising means, coupled to the transmit beamformer, for synchronizing one ultrasonic beam transmission with a predicted future occurrence of a selected event in a reference signal and performing another ultrasonic beam transmission at a selected time interval preceding the predicted future occurrence.

* * * * *

UNITED STATES PATENT AND TRADEMARK OFFICE
CERTIFICATE OF CORRECTION

PATENT NO. : 5,935,069
DATED : August 10, 1999
INVENTOR(S) : Paul e. Chandler, et. al.

It is certified that error appears in the above-identified patent and that said Letters Patent is hereby corrected as shown below:

On the Title Page

Page 2, column 2, line 1, please change "Remodeling" to --Modeling--.

Page 2, column 2, line 4, please change "Chiang c. Mei" to --Chiang C. Mei--.

In column 5, lines 34 and 37, please change "R wave" to --R-wave--.

In column 6, line 11, please change "perform" to --performing--.

In claim 1, line 8, please change "fixture" to --future--.

Signed and Sealed this

Sixth Day of February, 2001

Attest:

Q. TODD DICKINSON

*Attesting Officer*  *Director of Patents and Trademarks*